United States Patent
Berger

(10) Patent No.: US 11,058,656 B2
(45) Date of Patent: Jul. 13, 2021

(54) LIPID FORMULATIONS CONTAINING BIOACTIVE FATTY ACIDS

(71) Applicant: SCIADONICS, INC., Long Lake, MN (US)

(72) Inventor: Alvin Berger, Long Lake, MN (US)

(73) Assignee: SCIADONICS, INC., Long Lake, MN (US)

( * ) Notice: Subject to any disclaimer, the term of this patent is extended or adjusted under 35 U.S.C. 154(b) by 0 days.

(21) Appl. No.: 15/778,969

(22) PCT Filed: Nov. 23, 2016

(86) PCT No.: PCT/US2016/063467
§ 371 (c)(1),
(2) Date: May 24, 2018

(87) PCT Pub. No.: WO2017/091647
PCT Pub. Date: Jun. 1, 2017

(65) Prior Publication Data
US 2018/0353453 A1    Dec. 13, 2018

Related U.S. Application Data

(60) Provisional application No. 62/363,425, filed on Jul. 18, 2016, provisional application No. 62/303,170, filed on Mar. 3, 2016, provisional application No. 62/259,785, filed on Nov. 25, 2015.

(51) Int. Cl.
*A61K 31/202* (2006.01)
*A23L 33/12* (2016.01)
*A61K 45/06* (2006.01)

(52) U.S. Cl.
CPC ............ *A61K 31/202* (2013.01); *A23L 33/12* (2016.08); *A61K 45/06* (2013.01); *A23V 2002/00* (2013.01)

(58) Field of Classification Search
CPC .............................. A61K 31/201; A61K 31/202
See application file for complete search history.

(56) References Cited

U.S. PATENT DOCUMENTS

| | | | |
|---|---|---|---|
| 5,456,912 | A | 10/1995 | German et al. |
| 6,280,755 | B1 | 8/2001 | Berger et al. |
| 2007/0281045 | A1 | 12/2007 | Tripp et al. |
| 2008/0114065 | A1 | 5/2008 | Pacioretty et al. |
| 2012/0156171 | A1 | 6/2012 | Breton et al. |
| 2012/0270845 | A1 | 10/2012 | Bannister et al. |

FOREIGN PATENT DOCUMENTS

| | | |
|---|---|---|
| JP | 6158536 | 3/1986 |
| JP | 5-91886 | 4/1993 |
| WO | 95/17897 | 7/1995 |
| WO | 96/005164 | 2/1996 |
| WO | 2014/143614 | 9/2014 |
| WO | 2017/048774 | 3/2017 |
| WO | 2017/106595 | 6/2017 |
| WO | 2018/017667 | 1/2018 |

OTHER PUBLICATIONS

International Search Report & Written Opinion, International Patent Application No. PCT/US2016/063467, dated Feb. 16, 2017, 17 pages.

*Primary Examiner* — Savitha M Rao
*Assistant Examiner* — Gregg Polansky
(74) *Attorney, Agent, or Firm* — Casimir Jones S.C.; J. Mitchell Jones

(57) ABSTRACT

Provided herein is technology relating to lipid compositions containing bioactive fatty acids and particularly, but not exclusively, to compositions containing defined ratios of 5,11,14-eicosatrienoic acid to one or more of: 5,9,12-octadecatrienoic acid; 7,11,14-eicosatrienoic acid; 5,8,11,14-eicosatetraenoic acid; 9,12-octadecadienoic acid; 9-octadecenoic acid; 14-methyl hexadecanoic acid; 11,14 eicosadienoic acid, 5,9-octadecadienoic acid; 5,11-octadecadienoic acid; 9,12,15-octadecatrienoic acid; 5,8,11,14,17-eicosapentaenoic acid; 7,10,13,16,19-docosapentaenoic acid; and 4,7,10,13,16,19-docosahexaenoic acid.

7 Claims, No Drawings

US 11,058,656 B2

LIPID FORMULATIONS CONTAINING BIOACTIVE FATTY ACIDS

CROSS-REFERENCE TO RELATED APPLICATIONS

This application is a 371 U.S. National Phase Entry of International Application No. PCT/US2016/063,467, filed Nov. 23, 2016, which claims the priority benefit of U.S. Provisional Application Ser. No. 62/259,785, filed Nov. 25, 2015, U.S. Provisional Application Ser. No. 62/303,170, filed Mar. 3, 2016, and U.S. Provisional Application Ser. No. 62/363,425, filed Jul. 18, 2016, which are incorporated herein by reference in their entireties.

FIELD OF TECHNOLOGY

Provided herein is technology relating to lipid compositions containing bioactive fatty acids and particularly, but not exclusively, to compositions containing defined ratios of 5,11,14-eicosatrienoic acid to one or more of: 5,9,12-octadecatrienoic acid; 7,11,14-eicosatrienoic acid; 5,8,11,14-eicosatetraenoic acid; 9,12-octadecadienoic acid; 9-octadecenoic acid; 11,14 eicosadienoic acid; 14-methylhexadecanoic acid; 5,9-octadecadienoic acid; 5,11-octadecadienoic acid; 9,12,15-octadecatrienoic acid; 5,8,11,14,17-eicosapentaenoic acid; 7,10,13,16,19-docosapentaenoic acid; and 4,7,10,13,16,19-docosahexaenoic acid.

BACKGROUND

Bioactive fatty acids have been implicated for the treatment of various diseases and conditions. Bioactive fatty acids from natural sources have formed the basis for many popular and successful dietary supplements including various fish oils.

A number of bioactive fatty acids from a variety of sources have been identified including sciadonic acid, pinolenic acid, eicosapentaenoic acid, docosahexaenoic acid, and conjugated linoleic acid, just to name a few. Additionally, non-β-oxidizable fatty acid analogues such as tetradecylthioacetic acid have been shown to have excellent bioactivity. However, the use of juniperonic acid (5, 11, 14, 17 (all cis) 20:4) as a dietary supplement has not been previously investigated.

What is needed in the art are improved compounds, compositions and formulations that enhance the usefulness of bioactive fatty acid for treating particular diseases and conditions.

SUMMARY

Provided herein is technology relating to lipid compositions containing bioactive fatty acids and particularly, but not exclusively, to compositions containing defined ratios of 5,11,14-eicosatrienoic acid to one or more of: 5,9,12-octadecatrienoic acid; 7,11,14-eicosatrienoic acid; 5,8,11,14-eicosatetraenoic acid; 9,12-octadecadienoic acid; 9-octadecenoic acid; 14-methylhexadecanoic acid; 5,9-octadecadienoic acid; 5,11-octadecadienoic acid; 9,12,15-octadecatrienoic acid; 5,8,11,14,17-eicosapentaenoic acid; 7,10,13,16,19-docosapentaenoic acid; and 4,7,10,13,16,19-docosahexaenoic acid.

In some embodiments, the present invention provides a lipid formulation comprising an effective amount of 5,11,14-eicosatrienoic acid, wherein the lipid formulation is suitable for human consumption and one or more of the following properties:

a) the formulation comprises 5, 9, 12-octadecatrienoic acid, wherein the ratio of 5,11,14-eicosatrienoic acid: 5,9,12-octadecatrienoic acid is selected from the group consisting of 1:1 to 10:1, 1:1 to 5:1, 1:1 to 3:1, 1.5:1 to 2.5:1, 1.8:1 to 2.2:1, 1:2 to 1:20, 1:2 to 1:10, and 1:2 to 1:7;

b) the formulation comprises 7,11,14-eicosatrienoic acid, wherein the ratio of 5,11,14-eicosatrienoic acid: 7,11,14-eicosatrienoic acid is selected from the group consisting of 3.5:1 to 6.5:1, 4:1 to 6:1, and 4.5:1 to 5.5:1;

c) the formulation comprises at least trace amounts of an acid selected from the group consisting of abietic acid, pimaric acid and/or 5,9,12,15-octadecatetraenoic acid, and preferably in combination with 5,11,14-eicosatrienoic acid, d) the formulation comprises 5,8,11,14-eicosatetraenoic acid, wherein the ratio of 5,11,14-eicosatrienoic acid: 5,8,11,14-eicosatetraenoic acid is selected from the group consisting of 1:1 to 25:1, 3:1 to 25:1, 10:1 to 25:1, 1:1 to 10:1, and 3:1 to 10:1;

e) the formulation comprises 14-methylhexadecanoic acid, wherein the ratio of 5,11,14-eicosatrienoic acid: 14-methylhexadecanoic acid is selected from the group consisting of 1:1 to 25:1, 1:1 to 10:1, 2:1 to 8:1, 3:1 to 7:1 and 4:1 to 6:1;

f) the formulation comprises 9,12-octadecadienoic acid, wherein the ratio of 5,11,14-eicosatrienoic acid: 9,12-octadecadienoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1;

g) the formulation comprises 9-octadecenoic acid, wherein the ratio of 5,11,14-eicosatrienoic acid: 9, 12-octadecadienoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1;

h) the formulation comprises 5, 9-octadecadienoic acid, wherein the ratio of 5,11,14-eicosatrienoic acid: 5, 9-octadecadienoic acid is selected from the group consisting of 1:1 to 1:10, 1:2 to 1:8, 1:3 to 1:7, and 1:4 to 1:6;

i) the formulation comprises 5, 11-octadecadienoic acid, wherein the ratio of 5,11,14-eicosatrienoic acid: 5,11-octadecadienoic acid is selected from the group consisting of 1:1 to 10:1, 1:1 to 5:1, 1:1 to 4:1, 1:1 to 3:1, 1:1 to 1:2:1, 1:2 to 5:1, and 1:2 to 1:4;

j) the formulation comprises 5,8,11,14,17-eicosapentaenoic acid, wherein the ratio of 5,11,14-eicosatrienoic acid: 5,8,11,14,17-eicosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1;

k) the formulation comprises 4,7,10,13,16,19-docosahexaenoic acid, wherein the ratio of 5,11,14-eicosatrienoic acid: 4,7,10,13,16,19-docosahexaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1;

l) the formulation comprises 7,10,13,16,19-docosapentaenoic acid, wherein the ratio of 5,11,14-eicosatrienoic acid: 7,10,13,16,19-docosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1;

m) the formulation comprises 11, 14 eicosadienoic acid (20:2 n-6), wherein the ratio of 5,11,14-eicosatrienoic acid to 11, 14 eicosadienoic acid (20:2 n-6) is selected from the group consisting of from 1:1 to 10:1, 1:1 to 5:1, 1:1 to 3:1, 1:1 to 2.5:1, 1.5: 1 to 5:1, 1.5:1 to 3:1, 1.5:1 to 2.5:1, and 1.5:1 to 2:1; and n) the formulation comprises gammalinolenic acid (6, 9, 12, 18:3) and/or dihommogammalinolenic acid (8,11,14, 20:3), wherein the ratio of 5,11,14-eicosatrienoic acid to gammalinolenic acid (6,9,12, 18:3) and/or dihommogammalinolenic acid (8,11,14, 20:3) is selected from the group consisting of from 1:1 to 10:1, 1:1 to 5:1, 1:1 to 3:1, 1:1 to 2.5:1, 1.5: 1 to 5:1, 1.5:1 to 3:1, 1.5:1 to 2.5:1, and 1.5:1 to 2:1.

In some embodiments, the lipid formulation has two or more of properties (a) to (l). In some embodiments, the lipid formulation has three or more of properties (a) to (l). In some embodiments, the lipid formulation has four or more of properties (a) to (l). In some embodiments, the lipid formulation has five or more of properties (a) to (l). In some embodiments, the lipid formulation has six or more of properties (a) to (l). In some embodiments, the lipid formulation has seven or more of properties (a) to (l). In some embodiments, the lipid formulation has eight or more of properties (a) to (l). In some embodiments, the lipid formulation has nine or more of properties (a) to (l). In some embodiments, the lipid formulation has ten or more of properties (a) to (l). In some embodiments, the lipid formulation has eleven or more of properties (a) to (l). In some embodiments, the lipid formulation has property (a). In some embodiments, the lipid formulation has property (b). In some embodiments, the lipid formulation has property (c). In some embodiments, the lipid formulation has properties (a) and (b). In some embodiments, the lipid formulation has properties (a), (b) and (c). In some embodiments, the lipid formulation has property (d). In some embodiments, the lipid formulation has property (e). In some embodiments, the lipid formulation has property (h). In some embodiments, the lipid formulation has property (i). In some embodiments, the lipid formulations additionally have property (f). In some embodiments, the lipid formulations additionally have property (g). In some embodiments, the lipid formulations additionally have at least one of properties selected from the group consisting of (j), (k) and (l). In some embodiments, the lipid formulation additionally have properties (f) and (g). In some embodiments, the lipid formulation additionally has at least one of properties selected from the group consisting of (j), (k) and (l). In some embodiments, the lipid formulation has property (m). In some embodiments, the lipid formulation has properties (e) and (m).

In some embodiments, the fatty acids in the lipid formulations are esterified to a triglyceride, diglyceride, or phospholipid molecule, or combinations thereof. In some embodiments, the fatty acids in the lipid formulations are esterified to a triglyceride or diglyceride molecule. In some embodiments, the fatty acids in the lipid formulations are provided as ethyl esters.

In some embodiments, the formulations further comprise an antioxidant.

In some embodiments, the fatty acids in the lipid formulation are obtained from at least two different sources. In some embodiments, the fatty acids in the lipid formulation are obtained from at least three different sources. In some embodiments, the fatty acids in the lipid formulation are obtained from two to five different sources.

In some embodiments, the present invention provides an oral delivery vehicle, topical formulation, food product, nutritional supplement, dietary supplement or functional food comprising a lipid formulation as described above.

In some embodiments, the present invention provides a method of treating a subject comprising administering to the subject a lipid formulation, oral delivery vehicle, topical formulation, food product, nutritional supplement, dietary supplement or functional food as described above to a subject in need thereof. In some embodiments, the administration is oral, topical, parenteral, enteral, transdermal, intradermal, intraocular, intravitreal, sublingual, or intravaginal.

In some embodiments, the present invention provides a method of reducing obesity, inducing weight loss, increasing lean body mass, increasing muscularity, increasing muscle mass, improving body composition, alleviating one or more symptoms metabolic syndrome, treating diabetes, decreasing insulin resistance, reducing inflammation, improving concentration, memory, cognitive function, attention and treating, alleviating or improving one or more of the following diseases or conditions: restenosis, arteriosclerosis, coronary heart disease, thrombosis, myocardial infarction, stroke, hypertension, fatty liver, diabetes, hyperglycaemia, hyperinsulinemia, and stenosis, rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegeners granulomatosis), inflammatory bowel diseases and colitis (e.g., Crohn's colitis), nephritis, various inflammatory skin disorders (e.g. psoriasis, atopic dermatitis and food allergy) and acute and chronic allograft rejection after organ transplantation, comprising: administering to a subject in need thereof a lipid formulation, oral delivery vehicle, topical formulation, food product, nutritional supplement, dietary supplement or functional food as described above.

In some embodiments, the present invention provides a method of treating diabetes, ameliorating the symptoms of diabetes, providing nutritional support to a subject with diabetes, promoting healthy blood sugar levels, supporting efficient insulin production and secretion, and supporting healthy glucose metabolism, comprising: administering to a subject in need thereof a lipid formulation, oral delivery vehicle, food product, nutritional supplement, dietary supplement or functional food as described above.

In some embodiments, the lipid formulations are suitable for human consumption on a daily basis for an extended period of time, e.g., 1 month, 2 months, 6 months, 1 year or 2 years, when provided in daily dosage of from 200 mg to 5 or 10 grams. In some embodiments, the lipid formulations further comprise a food safe antioxidant. In some embodiments, the lipid formulations are provided in an oral delivery vehicle, food product, nutritional supplement, dietary supplement or functional food.

The present invention likewise provides methods of using the lipid formulations. These methods and uses are described in detail below but may be summarized as follows. In some embodiments, the present invention provides methods of treating a subject comprising administering to the subject the bioactive lipid formulation or oral delivery vehicle, topical formulation, food product, nutritional supplement, dietary supplement or functional food comprising the lipid formulation to a subject in need thereof. In some embodiments, the administration is oral, topical, parenteral, enteral, transdermal, intradermal, intraocular, intravitreal, sublingual, or intravaginal and may preferably comprise an effective amount of the composition.

In further preferred embodiments, the present invention provides methods of reducing obesity, inducing weight loss, increasing lean body mass, increasing muscularity, increasing muscle mass, improving body composition, alleviating one or more symptoms metabolic syndrome, treating diabetes, decreasing insulin resistance, reducing inflammation, improving concentration, memory, cognitive function, attention and treating, alleviating or improving one or more of the following diseases or conditions: restenosis, arteriosclerosis, coronary heart disease, thrombosis, myocardial infarction, stroke, hypertension, fatty liver, diabetes, hyperglycaemia, hyperinsulinemia, and stenosis, rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myasthenia gravis), various cardiovascular disorders (e.g. myocarditis, congestive heart failure, arteriosclerosis and stable and unstable angina, and Wegeners granulomatosis), inflammatory bowel diseases and colitis (e.g., Crohn's colitis), nephritis, various inflammatory skin disorders (e.g. psoriasis, atopic dermatitis and food allergy) and acute and chronic allograft rejection after organ transplantation, comprising administering to a subject in need thereof the bioactive lipid composition, structured phospholipid composition or structured acylglyceride composition or oral delivery vehicle, food product, nutritional supplement, dietary supplement or function food as described above. In some embodiments, the administration or oral, topical, parenteral, enteral, transdermal, intradermal, intraocular, intravitreal, sublingual, or intravaginal and may preferably comprise an effective amount of the composition. The treatment is preferably performed under conditions such that the disease or condition is alleviated or improved as compared to an untreated state.

In some embodiments, the methods comprise co-administration of a delta-6 desaturase inhibitor.

Additional embodiments will be apparent to persons skilled in the relevant art based on the teachings contained herein.

DETAILED DESCRIPTION

Provided herein is technology relating to lipid compositions containing bioactive fatty acids and particularly, but not exclusively, to compositions containing defined ratios of 5,11,14-eicosatrienoic acid to one or more of: 5,9,12-octadecatrienoic acid; 7,11,14-eicosatrienoic acid; 5,8,11,14-eicosatetraenoic acid; 9,12-octadecadienoic acid; 9-octadecenoic acid; 14-methylhexadecanoic acid; 5,9-octadecadienoic acid; 5,11-octadecadienoic acid; 9,12,15-octadecatrienoic acid; 5,8,11,14,17-eicosapentaenoic acid; 7,10,13,16,19-docosapentaenoic acid; and 4,7,10,13,16,19-docosahexaenoic acid.

This technology is described below, wherein the section headings are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, "feeding" refers to providing a substance, compound, composition, etc. to a living organism. For example, the substance, compound, composition, etc. may be an energy source, a carbon source, a nutrient, or a source of other elements, molecules, and/or precursors of biological molecules that are used by the living organism and/or are metabolized (e.g., catabolized, anabolized) by the living organism. The substance, compound, composition, etc. is not necessarily a substance, compound, composition, etc. that the living organism encounters in its native milieu, but may be a synthetic substance, compound, composition, etc. or a natural substance, compound, composition, etc. that is nevertheless used by the living organism for metabolism. The substance, compound, composition, etc. may be added to a culture medium or a substrate in which or on which the living organism lives and/or grows.

As used herein, "active" or "activity" refers to native or naturally occurring biological and/or immunological activity.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the terms "subject" and "patient" refer to any animal, such as a mammal like a dog, cat, bird, livestock, and preferably a human (e.g., a human with a disease such as obesity, diabetes, or insulin resistance).

As used herein, the term "individual" refers to vertebrates, particularly members of the mammalian species. The term includes but is not limited to domestic animals, sports animals, primates, and humans.

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent.

As used herein, the term "pharmaceutical composition" refers to the combination of an active agent with a carrier, inert or active, making the composition especially suitable for therapeutic use. The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present technology.

Embodiments of the Technology

Provided herein is technology relating to lipid compositions containing bioactive fatty acids and particularly, but not exclusively, to compositions containing defined ratios of 5,11,14-eicosatrienoic acid to one or more of: 5,9,12-octadecatrienoic acid; 7,11,14-eicosatrienoic acid; 5,8,11,14-eicosatetraenoic acid; 9,12-octadecadienoic acid; 9-octadecenoic acid; 14-methylhexadecanoic acid; 11,14 eicosadienoic acid (20:2 n-6, dihomolinoleic acid), 5,9-octadecadienoic acid; 5,11-octadecadienoic acid; 9,12,15-octadecatrienoic acid; 5,8,11,14,17-eicosapentaenoic acid; 7,10,13,16,19-docosapentaenoic acid; 4,7,10,13,16,19-docosahexaenoic acid, and gammalinolenic acid (6, 9, 12, 18:3) and/or dihommogammalinolenic acid (8,11,14, 20:3).

The present invention provides bioactive lipid formulations comprising one or more bioactive fatty acids, and in particularly preferred embodiments sciadonic acid in combination with other bioactive fatty acids. It will be understood that the fatty acids may be provided in the formulation as free fatty acids, as ethyl esters, or in the form of diglycerides, triglycerides, or phospholipids to which the fatty acid is attached. The bioactive lipid formulations are preferably characterized by comprising a particular ratio of the bioactive fatty acids to one another.

Thus, the lipid formulations according to the present technology are either fatty acids analogous to naturally occurring fatty acids, especially sciadonic acid and its analogs, alone in combination with other bioactive fatty acids, or naturally occurring lipids comprising the fatty acids. Incorporation of the fatty acids in naturally occurring lipids (e.g., monoglycerides, diglycerides, triglycerides, and/or phospholipids) produces a compound with different absorption characteristics compared to free fatty acids. In addition, it is contemplated that incorporating fatty acids in naturally occurring lipids (e.g., monoglycerides, diglycerides, triglycerides, and/or phospholipids) may also increase the bioavailability or stability.

The fatty acids utilized in the formulations may be provided from a number of natural sources. Suitable sources include, but are not limited to, various plant and animal sources such as sunflower oil, soybean oil, rapeseed oil, safflower oil, corn oil, olive oil, pine nut oil, tall oil, oils prepared from the seeds and fruits of *Juniperis* spp., *Torreya* spp., *Nageia* spp., *Taxus* spp., *Gingko* spp., *Araucaria* spp., and *Ephedra* spp., fish oils (herring oil, squid oil, salmon oil, tuna oil, anchovy oil, mackerel oil, cod liver oil, sardine oil, and the like), krill oil, Calanus oil, seal oil, algal oils, bacterial oils, green lipped mussel oil, and the like.

Accordingly, in some embodiments, the present invention provides a lipid formulation comprising lipids characterized in comprising an effective amount of 5,11,14-eicosatrienoic acid, wherein said lipid formulation is suitable for human consumption and is combined with at least a second bioactive fatty acid or agent in a defined ratio to the 5,11,14-eicosatrienoic acid component. One or more of the following fatty acid components or acids are preferably combined with 5,11,14-eicosatrienoic acid in the stated ratios to provide a lipid formulation of the present invention. In some embodiments, lipids extracted from different sources are combined to provide the defined fatty acid ratios in the lipid formulations. In some embodiments, the fatty acids in the lipid formulation are obtained from at least two different sources. In some embodiments, the fatty acids in the lipid formulation are obtained from at least three different sources. In some embodiments, the fatty acids in the lipid formulation are obtained from two to five different sources.

In some embodiments, the formulations comprise 5,11,14-eicosatrienoic acid and 5,9,12-octadecatrienoic acid, wherein the ratio of 5,11,14-eicosatrienoic acid: 5,9,12-octadecatrienoic acid is selected from the group consisting of 1:1 to 10:1, 1:1 to 5:1, 1:1 to 3:1, 1.5:1 to 2.5:1, 1.8:1 to 2.2:1, 1:2 to 1:20, 1:2 to 1:10, and 1:2 to 1:7.

In some embodiments, the formulations comprise 5,11,14-eicosatrienoic acid and 7,11,14-eicosatrienoic acid, wherein the ratio of 5,11,14-eicosatrienoic acid: 7,11,14-eicosatrienoic acid is selected from the group consisting of 3.5:1 to 6.5:1, 4:1 to 6:1, and 4.5:1 to 5.5:1.

In some embodiments, the formulations comprise at least trace amounts of an acid selected from the group consisting of abietic acid and pimaric acid.

In some embodiments, the formulations comprise 5,11,14-eicosatrienoic acid and 5,8,11,14-eicosatetraenoic acid, wherein the ratio of 5,11,14-eicosatrienoic acid: 5,8,11,14-eicosatetraenoic acid is selected from the group consisting of 1:1 to 25:1, 3:1 to 25:1, 10:1 to 25:1, 1:1 to 10:1, and 3:1 to 10:1.

In some embodiments, the formulations comprise 5,11,14-eicosatrienoic acid and 14-methylhexadecanoic acid, wherein the ratio of 5,11,14-eicosatrienoic acid: 14-methylhexadecanoic acid is selected from the group consisting of 1:1 to 25:1, 1:1 to 10:1, 2:1 to 8:1, 3:1 to 7:1 and 4:1 to 6:1.

In some embodiments, the formulations comprise 5,11,14-eicosatrienoic acid and 11, 14 eicosadienoic acid (20:2 n-6), wherein the ratio of 5, 11,14-eicosatrienoic acid to 11, 14 eicosadienoic acid (20:2 n-6) is from 1:1 to 10:1, 1:1 to 5:1, 1:1 to 3:1, 1:1 to 2.5:1, 1.5: 1 to 5:1, 1.5:1 to 3:1, 1.5:1 to 2.5:1, and 1.5:1 to 2:1. In some embodiments, the formulations comprise 5,11,14-eicosatrienoic acid and 9,12-octadecadienoic acid, wherein the ratio of 5,11,14-eicosatrienoic acid: 9,12-octadecadienoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1.

In some embodiments, the formulations comprise 5,11,14-eicosatrienoic acid and 9-octadecenoic acid, wherein the ratio of 5,11,14-eicosatrienoic acid: 9-octadecenoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1.

In some embodiments, the formulations comprise 5,11,14-eicosatrienoic acid and 5, 9-octadecadienoic acid, wherein the ratio of 5,11,14-eicosatrienoic acid: 5, 9-octadecadienoic acid is selected from the group consisting of 1:1 to 1:10, 1:2 to 1:8, 1:3 to 1:7, and 1:4 to 1:6.

In some embodiments, the formulations comprise 5,11,14-eicosatrienoic acid and 5,11-octadecadienoic acid, wherein the ratio of 5,11,14-eicosatrienoic acid: 5,11-octadecadienoic acid is selected from the group consisting of 1:1 to 10:1, 1:1 to 5:1, 1:1 to 4:1, 1:1 to 3:1, 1:1 to 1:2:1, 1:2 to 5:1, and 1:2 to 1:4.

In some embodiments, the formulations comprise 5,11,14-eicosatrienoic acid and 5,8,11,14,17-eicosapentaenoic acid, wherein the ratio of 5,11,14-eicosatrienoic acid: 5,8,11,14,17-eicosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the formulations comprise 5,11,14-eicosatrienoic acid and 4,7,10,13,16,19-docosahexaenoic acid, wherein the ratio of 5,11,14-eicosatrienoic acid: 4,7,10,13,16,19-docosahexaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the formulations comprise 5,11,14-eicosatrienoic acid and 7,10,13,16,19-docosapentaenoic acid, wherein the ratio of 5,11,14-eicosatrienoic acid: 7,10,13,16,19-docosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the lipid formulation preferably comprise 2, 3, 4, 5, 6, 7, 8, 9, 10, 11 or 2 or more, 3 or more, 4 or more, 5 or more, 6 or more, 7 or more, 8 or more, 9 or more, 10 or more or 11 or more of the fatty acids listed above in the defined ratios to 5,11,14-eicosatrienoic acid. The following are non-limiting examples of preferred formulations.

In some embodiments, the formulations comprise 5,11,14-eicosatrienoic acid and 5,9,12-octadecatrienoic acid, wherein the ratio of 5,11,14-eicosatrienoic acid: 5, 9, 12-octadecatrienoic acid is selected from the group consisting of 1:1 to 10:1, 1:1 to 5:1, 1:1 to 3:1, 1.5:1 to 2.5:1, 1.8:1 to 2.2:1, 1:2 to 1:20, 1:2 to 1:10, and 1:2 to 1:7 and 7, 11, 14-eicosatrienoic acid, wherein the ratio of 5,11,14-eicosatrienoic acid: 7,11,14-eicosatrienoic acid is selected from the group consisting of 3.5:1 to 6.5:1, 4:1 to 6:1, and 4.5:1 to 5.5:1.

In some embodiments, the formulations comprise 5,11,14-eicosatrienoic acid and 5,9,12-octadecatrienoic acid, wherein the ratio of 5,11,14-eicosatrienoic acid: 5,9,12-octadecatrienoic acid is selected from the group consisting of 1:1 to 10:1, 1:1 to 5:1, 1:1 to 3:1, 1.5:1 to 2.5:1, 1.8:1 to 2.2:1, 1:2 to 1:20, 1:2 to 1:10, and 1:2 to 1:7, 7, 11, 14-eicosatrienoic acid, wherein the ratio of 5,11,14-eicosatrienoic acid: 7,11,14-eicosatrienoic acid is selected from the group consisting of 3.5:1 to 6.5:1, 4:1 to 6:1, and 4.5:1 to 5.5:1, and at least trace amounts of an acid selected from the group consisting of abietic acid and pimaric acid.

In some embodiments, the formulations comprise 5,11,14-eicosatrienoic acid and 5,9,12-octadecatrienoic acid, wherein the ratio of 5,11,14-eicosatrienoic acid: 5,9,12-octadecatrienoic acid is selected from the group consisting of 1:1 to 10:1, 1:1 to 5:1, 1:1 to 3:1, 1.5:1 to 2.5:1, 1.8:1 to 2.2:1, 1:2 to 1:20, 1:2 to 1:10, and 1:2 to 1:7, 7, 11, 14-eicosatrienoic acid, wherein the ratio of 5,11,14-eicosatrienoic acid: 7,11,14-eicosatrienoic acid is selected from the group consisting of 3.5:1 to 6.5:1, 4:1 to 6:1, and 4.5:1 to 5.5:1, 9, 12-octadecadienoic acid, wherein the ratio of 5,11,14-eicosatrienoic acid: 9,12-octadecadienoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1, and 9-octadecenoic acid, wherein the ratio of 5,11,14-eicosatrienoic acid: 9-octadecenoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1. In some embodiments, these formulations optionally comprise at least one of 5,8,11,14,17-eicosapentaenoic acid, 4,7,10,13,16,19-docosahexaenoic acid, and/or 7,10,13,16,19-docosapentaenoic acid, wherein the ratio of 5,11,14-eicosatrienoic acid: 5,8,11,14,17-eicosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, wherein the ratio of 5,11,14-eicosatrienoic acid: 4,7,10,13,16,19-docosahexaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, and wherein the ratio of 5,11,14-eicosatrienoic acid: 7,10,13,16,19-docosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the formulations comprise 5,11,14-eicosatrienoic acid and 5,8,11,14-eicosatetraenoic acid, wherein the ratio of 5,11,14-eicosatrienoic acid: 5,8,11,14-eicosatetraenoic acid is selected from the group consisting of 1:1 to 25:1, 3:1 to 25:1, 10:1 to 25:1, 1:1 to 10:1, and 3:1 to 10:1, and one or both of 9,12-octadecadienoic acid and 9-octadecenoic acid wherein the ratio of 5,11,14-eicosatrienoic acid: 9,12-octadecadienoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1, and wherein the ratio of 5,11,14-eicosatrienoic acid: 9-octadecenoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1. In some embodiments, these formulations optionally comprise at least one of 5,8,11,14,17-eicosapentaenoic acid, 4,7,10,13,16,19-docosahexaenoic acid, and/or 7,10,13,16,19-docosapentaenoic acid, wherein the ratio of 5,11,14-eicosatrienoic acid: 5,8,11,14,17-eicosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, wherein the ratio of 5,11,14-eicosatrienoic acid: 4,7,10,13,16,19-docosahexaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, and wherein the ratio of 5,11,14-eicosatrienoic acid: 7,10,13,16,19-docosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the formulations comprise 5,11,14-eicosatrienoic acid, 14-methylhexadecanoic acid and 11, 14 eicosadienoic acid (20:2 n-6), wherein the ratio of 11,14-eicosatrienoic acid to 11, 14 eicosadienoic acid (20:2 n-6) is from 1:1 to 10:1, 1:1 to 5:1, 1:1 to 3:1, 1:1 to 2.5:1, 1.5: 1 to 5:1, 1.5:1 to 3:1, 1.5:1 to 2.5:1, and 1.5:1 to 2:1 and wherein the ratio of 5,11,14-eicosatrienoic acid: 14-methylhexadecanoic acid is selected from the group consisting of 1:1 to 25:1, 1:1 to 10:1, 2:1 to 8:1, 3:1 to 7:1 and 4:1 to 6:1.

In some embodiments, the formulations comprise 5,11,14-eicosatrienoic acid and 11, 14 eicosadienoic acid (20:2 n-6), wherein the ratio of 5, 11,14-eicosatrienoic acid to 11, 14 eicosadienoic acid (20:2 n-6) is from 1:1 to 10:1, 1:1 to 5:1, 1:1 to 3:1, 1:1 to 2.5:1, 1.5: 1 to 5:1, 1.5:1 to 3:1, 1.5:1 to 2.5:1, and 1.5:1 to 2:1 and one or both of 9,12-octadecadienoic acid and 9-octadecenoic acid wherein the ratio of 5,11,14-eicosatrienoic acid: 9,12-octadecadienoic acid is selected from the group consisting of 1:1 to 1:25, 1:1 to 1:10, 1:1 to 1:5, 1:1 to 1:3 and 1:1 to 2.5:1, and wherein the ratio of 5,11,14-eicosatrienoic acid: 9-octadecenoic acid is selected from the group consisting of 1:5 to 5:1, 1:4 to 4:1, 1:3 to 3:1, 1:2 to 2:1, and 1:1.5 and 1.5:1. In some embodiments, these formulations optionally comprise at least one of 5,8,11,14,17-eicosapentaenoic acid, 4,7,10,13,16,19-docosahexaenoic acid, and/or 7,10,13,16,19-docosapentaenoic acid, wherein the ratio of 5,11,14-eicosatrienoic acid: 5,8,11,14,17-eicosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, wherein the ratio of 5,11,14-eicosatrienoic acid: 4,7,10,13,16,19-docosahexaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, and wherein the ratio of 5,11,14-eicosatrienoic acid: 7,10,13,16,19-docosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the formulations comprise 5,11,14-eicosatrienoic acid and 14-methylhexadecanoic acid, wherein the ratio of 5,11,14-eicosatrienoic acid: 14-methylhexadecanoic acid is selected from the group consisting of 1:1 to 25:1, 1:1 to 10:1, 2:1 to 8:1, 3:1 to 7:1 and 4:1 to 6:1 and one or both of 9,12-octadecadienoic acid and 9-octadecenoic acid wherein the ratio of 5,11,14-eicosatrienoic acid: 9,12-octadecadienoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1, and wherein the ratio of 5,11,14-eicosatrienoic acid: 9-octadecenoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1. In some embodiments, these formulations optionally comprise at least one of 5,8,11,14,17-eicosapentaenoic acid, 4,7,10,13,16,19-docosahexaenoic acid, and/or 7,10,13,16,19-docosapentaenoic acid, wherein the ratio of 5,11,14-eicosatrienoic acid: 5,8,11,14,17-eicosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, wherein the ratio of 5,11,14-eicosatrienoic acid: 4,7,10,13,16,19-docosahexaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, and wherein the ratio of 5,11,14-eicosatrienoic acid: 7,10,13,16,19-docosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the formulations comprise 5,11,14-eicosatrienoic acid and 5,9-octadecadienoic acid, wherein the ratio of 5,11,14-eicosatrienoic acid: 5,9-octadecadienoic acid is selected from the group consisting of 1:1 to 1:10, 1:2 to 1:8, 1:3 to 1:7, and 1:4 to 1:6 and one or both of 9,12-octadecadienoic acid and 9-octadecenoic acid wherein the ratio of 5,11,14-eicosatrienoic acid: 9,12-octadecadienoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1, and wherein the ratio of 5,11,14-eicosatrienoic acid: 9-octadecenoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1. In some embodiments, these formulations optionally comprise at least one of 5,8,11,14,17-eicosapentaenoic acid, 4,7,10,13,16,19-docosahexaenoic acid, and/or 7,10,13,16,19-docosapentaenoic acid, wherein the ratio of 5,11,14-eicosatrienoic acid: 5,8,11,14,17-eicosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, wherein the ratio of 5,11,14-eicosatrienoic acid: 4,7,10,13,16,19-docosahexaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, and wherein the ratio of 5,11,14-eicosatrienoic acid: 7,10,13,16,19-docosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the formulations comprise 5,11,14-eicosatrienoic acid and 5,11-octadecadienoic acid, wherein the ratio of 5,11,14-eicosatrienoic acid: 5,11-octadecadienoic acid is selected from the group consisting of 1:1 to 10:1, 1:1 to 5:1, 1:1 to 4:1, 1:1 to 3:1, 1:1 to 1:2:1, 1:2 to 5:1, and 1:2 to 1:4 and one or both of 9,12-octadecadienoic acid and 9-octadecenoic acid wherein the ratio of 5,11,14-eicosatrienoic acid: 9,12-octadecadienoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1, and wherein the ratio of 5,11,14-eicosatrienoic acid: 9-octadecenoic acid is selected from the group consisting of 1:1 to 25:1, 2:1 to 25:1, 5:1 to 25:1, 10:1 to 25:1, 1:1 to 20:1, 2:1 to 20:1, 5:1 to 20:1, 10:1 to 20:1, 1:1 to 10:1, 2:1 to 10:1, and 5:1 to 10:1. In some embodiments, these formulations optionally comprise at least one of 5,8,11,14,17-eicosapentaenoic acid, 4,7,10,13,16,19-docosahexaenoic acid, and/or 7,10,13,16,19-docosapentaenoic acid, wherein the ratio of 5,11,14-eicosatrienoic acid: 5,8,11,14,17-eicosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, wherein the ratio of 5,11,14-eicosatrienoic acid: 4,7,10,13,16,19-docosahexaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1, and wherein the ratio of 5,11,14-eicosatrienoic acid: 7,10,13,16,19-docosapentaenoic acid is selected from the group consisting of 20:1 to 1:20, 10:1 to 1:10, 5:1 to 1:5, 3:1 to 1:3, 1:1 to 1:20, 1:1 to 1:10, 1:1 to 1:5, 1:1 to 1:3, 20:1 to 1:1, 10:1 to 1:1, 5:1 to 1:1, and 3:1 to 1:1.

In some embodiments, the formulations comprise gammalinolenic acid (6, 9,12, 18:3) and/or dihommogammalinolenic acid (8,11,14, 20:3), wherein the ratio of 5,11,14-eicosatrienoic acid to gammalinolenic acid (6,9,12, 18:3) and/or dihommogammalinolenic acid (8,11,14, 20:3) is selected from the group consisting of from 1:1 to 10:1, 1:1 to 5:1, 1:1 to 3:1, 1:1 to 2.5:1, 1.5:1 to 5:1, 1.5:1 to 3:1, 1.5:1 to 2.5:1, and 1.5:1 to 2:1.

In some embodiments, the fatty acids in the lipid formulation are esterified to a triglyceride, diglyceride, monoglyceride or phospholipid molecule. In some embodiments, the fatty acids in the lipid formulation are provided as ethyl esters.

In some embodiments, the lipid formulations further comprise a delta-6 desaturase inhibitor. The present invention is not limited to any particular delta-6 desaturase inhibitor. In some embodiments, the delta-6 desaturase inhibitor is 2,2-diphenyl-5-(4-[[(1 E)-pyridin-3-yl-methylidene]amino]piperazin-1-yl)pentanenitrile (SC-26196).

In some embodiments, the lipid formulations are suitable for human consumption on a daily basis for an extended period of time, e.g., 1 month, 2 months, 6 months, 1 year or 2 years, when provided in daily dosage of from 200 mg to 5 or 10 grams. In some embodiments, the lipid formulations further comprise a food safe antioxidant. In some embodiments, the lipid formulations are provided in an oral delivery vehicle, topical formulation, pharmaceutical formulation, food product, nutritional supplement, dietary supplement or functional food.

Provided herein are pharmaceutical compositions comprising a therapeutically effective amount of a lipid formulation according to the present technology and a pharmaceutically acceptable carrier, diluent, or excipient (including combinations thereof).

A composition according to the technology comprises or consists of a therapeutically effective amount of a the lipid formulation. In some embodiments, it includes a pharmaceutically acceptable carrier, diluent, or excipient (including combinations thereof). Acceptable carriers or diluents for therapeutic use are well known in the pharmaceutical art and are described, for example, in Remington's Pharmaceutical Sciences, Mack Publishing Co. (A. R. Gennaro edit. 1985). The choice of pharmaceutical carrier, excipient, or diluent is selected with regard to the intended route of administration and standard pharmaceutical practice. The pharmaceutical comprise as, or in addition to, the carrier, excipient, or diluent any suitable binder(s), lubricant(s), suspending agent (s), coating agent(s), and/or solubilizing agent(s).

This pharmaceutical composition will desirably be provided in a sterile form. It may be provided in unit dosage form and will generally be provided in a sealed container. A plurality of unit dosage forms may be provided.

Pharmaceutical compositions within the scope of the present technology may include one or more of the following: preserving agents, solubilizing agents, stabilizing agents, wetting agents, emulsifiers, sweeteners, colorants, flavoring agents, odorants, and/or salts. Compounds of the present technology may themselves be provided in the form of a pharmaceutically acceptable salt. In addition, embodiments may comprise buffers, coating agents, antioxidants, suspending agents, adjuvants, excipients, and/or diluents. Examples of preservatives include sodium benzoate, sorbic acid, and esters of p-hydroxybenzoic acid.

They may also contain other therapeutically active agents in addition to compounds of the present technology. Where two or more therapeutic agents are used they may be administered separately (e.g., at different times and/or via different routes) and therefore do not always need to be present in a single composition. Thus, combination therapy is within the scope of the present technology.

A pharmaceutical composition within the scope of the present technology may be adapted for administration by any appropriate route. For example, it may be administered by the oral (including buccal or sublingual), rectal, nasal, topical (including buccal, sublingual, or transdermal), vaginal, or parenteral (including subcutaneous, intramuscular, intravenous, or intradermal) routes. Such a composition may be prepared by any method known in the art of pharmacy, for example, by admixing one or more active ingredients with a suitable carrier.

In various embodiments, different drug delivery systems are used to administer pharmaceutical compositions of the present technology, depending upon the desired route of administration. Drug delivery systems are described, for example, by Langer (*Science* 249:1527-1533 (1991)) and by Illum and Davis (*Current Opinions in Biotechnology* 2: 254-259 (1991)).

The agents of the present technology may be administered alone but will generally be administered as a pharmaceutical composition—e.g., the agent is in admixture with a suitable pharmaceutical excipient, diluent, or carrier selected with regard to the intended route of administration and standard pharmaceutical practice. For example, in some embodiments the agent is administered (e.g., orally or topically) in the form of tablets, capsules, ovules, elixirs, solutions, or suspensions, which may contain flavoring or coloring agents, for immediate, delayed, modified, sustained, pulsed, and/or controlled-release applications.

In some embodiments, tablets contain excipients such as microcrystalline cellulose, lactose, sodium citrate, calcium carbonate, dibasic calcium phosphate and/or glycine; disintegrants such as starch (preferably corn, potato, or tapioca starch), sodium starch glycollate, croscarmellose sodium, and/or certain complex silicates; and/or granulation binders such as polyvinylpyrrolidone, hydroxypropylmethylcellulose (HPMC), hydroxypropylcellulose (HPC), sucrose, gelatin, and/or acacia. Additionally, lubricating agents such as magnesium stearate, stearic acid, glyceryl behenate, and talc may be included.

In some embodiments, solid compositions of a similar type are also employed as fillers in gelatin capsules. Examples of excipients in this regard include lactose, starch, a cellulose, milk sugar, or high molecular weight polyethylene glycols. For some embodiments of aqueous suspensions and/or elixirs, the agent is combined with various sweetening or flavoring agents, coloring matter or dyes, with emulsifying and/or suspending agents and with diluents such as water, ethanol, propylene glycol, and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, via the penis, vaginal, epidural, sublingual.

It is to be understood that not all of the agent need be administered by the same route. Likewise, if the composition comprises more than one active component, then those components may be administered by different routes.

If the agent of the present technology is administered parenterally, then examples of such administration include one or more of: intravenously, intra-arterially, intraperitoneally, intrathecally, intraventricularly, intraurethrally, intrasternally, intracranially, intramuscularly, or subcutaneously administering the agent; and/or by using infusion techniques.

In some embodiments, pharmaceutical compositions adapted for oral administration are provided as capsules or tablets; as powders or granules; as solutions, syrups or suspensions (in aqueous or non-aqueous liquids); as edible foams or whips; or as emulsions. Tablets or hard gelatine capsules may comprise lactose, maize starch or derivatives thereof, stearic acid or salts thereof. Soft gelatine capsules may comprise vegetable oils, waxes, fats, semi-solid, or liquid polyols etc. Solutions and syrups may comprise water, polyols and sugars. For the preparation of suspensions, oils (e.g., vegetable oils) may be used to provide oil-in-water or water-in-oil suspensions. An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. For example, the active ingredient may be delivered from the patch by iontophoresis, e.g., as described in *Pharmaceutical Research*, 3: 318 (1986)).

Alternatively, the agent of the present technology can be administered in the form of a suppository or pessary, or it may be applied topically in the form of a gel, hydrogel, lotion, solution, cream, ointment or dusting powder. The agent of the present technology may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present technology can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Pharmaceutical compositions adapted for rectal administration may be provided as suppositories or enemas.

Pharmaceutical compositions adapted for nasal administration may use solid carriers, e.g., powders (e.g., having a particle size in the range of 20 to 500 microns). Powders can be administered in the manner in which snuff is taken, e.g., by rapid inhalation through the nose from a container of powder held close to the nose. Compositions adopted for nasal administration may alternatively use liquid carriers, e.g., nasal sprays or nasal drops. These may comprise aqueous or oil solutions of the active ingredient. Compositions for administration by inhalation may be supplied in specially adapted devices, e.g., in pressurized aerosols, nebulizers, or insufflators. These devices can be constructed so as to provide predetermined dosages of the active ingredient Pharmaceutical compositions adapted for vaginal administration may be provided as pessaries, tampons, creams, gels, pastes, foams or spray formulations.

If the agent of the present technology is administered parenterally, then examples of such administration include one or more of: intravenously, intra-arterially, intraperitoneally, intrathecally, intraventricularly, intraurethrally, intrasternally, intracranially, intramuscularly or subcutaneously administering the agent; and/or by using infusion techniques. For parenteral administration, the agent is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

"Transdermal" refers to the delivery of a compound by passage through the skin and into the blood stream. "Transmucosal" refers to delivery of a compound by passage of the compound through the mucosal tissue and into the blood stream. "Transurethral" or "intraurethral" refers to delivery of a drug into the urethra, such that the drug contacts and passes through the wall of the urethra and enters into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

Penetration enhancers may include, for example, dimethylsulfoxide (DMSO); dimethyl formamide (DMF); N,N-dimethylacetamide (DMA); decylmethylsulfoxide (CI-OMSO); polyethyleneglycol monolaurate (PEGML); glyceral monolaurate; lecithin; 1-substituted azacycloheptanones, particularly 1-N-dodecylcyclaza-cycloheptanones (e.g., as available under the trademark Azone™ from Nelson Research & Development Co., Irvine, Calif.), alcohols, and the like.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

Examples of pharmaceutically acceptable carriers include, for example, water, salt solutions, alcohol, silicone, waxes, petroleum jelly, vegetable oils, polyethylene glycols, propylene glycol, sugars, gelatin, lactose, amylose, magnesium stearate, talc, surfactants, silicic acid, viscous paraffin, perfume oil, fatty acid monoglycerides and diglycerides, petroethral fatty add esters, hydroxymethyl-cellulose, polyvinylpyrrolidone, and the like.

Typically, a physician will determine the actual dosage which will be most suitable for an individual subject. The specific dose level and frequency of dosage for any particular patient may be varied and will depend upon a variety of factors including the activity of the specific compound employed; the metabolic stability and length of action of that compound; the age, body weight, general health, sex, diet, mode and time of administration; rate of excretion; drug combination; the severity of the particular condition; and the individual undergoing therapy. The agent and/or the pharmaceutical composition of the present technology may be administered in accordance with a regimen of from 1 to 10 times per day, such as once or twice per day. For oral and parenteral administration to human patients, the daily dosage level of the agent may be in single or divided doses.

Depending upon the need, the agent may be administered at a dose of from 0.01 to 30 mg/kg body weight, such as from 0.1 to 10 mg/kg or from 0.1 to 1 mg/kg body weight. Naturally, the dosages mentioned herein are exemplary of the average case. There can, of course, be individual instances where higher or lower dosage ranges are merited.

"Therapeutically effective amount" refers to the amount of the therapeutic agent that is effective to achieve its intended purpose. While individual patient needs may vary, determination of optimal ranges for effective amounts of the compounds related to the technology is within the skill of the art. Generally, the dosage regimen for treating a condition with the compounds and/or compositions of this technology is selected in accordance with a variety of factors, including the type, age, weight, sex, diet and medical condition of the patient; the severity of the dysfunction; the route of administration; pharmacological considerations such as the activity, efficacy, pharmacokinetic and toxicology profiles of the particular compound used; whether a drug delivery system is used; and whether the compound is administered as part of a drug combination and can be adjusted by one skilled in the art. Thus, the dosage regimen actually employed may vary widely and therefore may deviate from the exemplary dosage regimens set forth herein.

In general, the lipid formulations may be used in combination with one or more other pharmaceutically active agents. Other agents are sometimes referred to auxiliary agents.

The fatty acids may be in the form of, and/or may be administered as, a pharmaceutically acceptable salt, e.g., an acid addition salt or a base salt, or a solvate thereof, including a hydrate thereof. For a review on suitable salts see Berge et al, *J.* (1977) *Pharm. Sci.* 66: 1-19.

Typically, a pharmaceutically acceptable salt may be readily prepared by using a desired acid or base, as appropriate. The salt may precipitate from solution and be collected by filtration or may be recovered by evaporation of the solvent.

Suitable acid addition salts are formed from acids that form non-toxic salts such as hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate, and pamoate salts.

Suitable base salts are formed from bases that form non-toxic salts and examples are sodium, potassium, aluminum, calcium, magnesium, zinc, and diethanolamine salts.

In some embodiments, the lipid formulations of this invention are contained in acceptable excipients and/or carriers for oral consumption as a dietary supplement. The actual form of the carrier, and thus, the composition itself, is not critical. The carrier may be a liquid, gel, gelcap, capsule, powder, solid tablet (coated or non-coated), tea, or the like. The lipid composition may be in the form of dry powders, granules, pills, tablets, capsules, lozenges, dry products for reconstitution with water or other suitable carrier, aqueous or oily solutions or suspensions, gels, pastes, emulsions or syrups.

The composition is preferably in the form of a tablet or capsule and most preferably in the form of a soft gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Mack Publishing Co., Easton, Pa.). In other embodiments, the composition contains no traces of organic solvents which is an important property regarding the safety of consuming such compounds.

In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The lipid formulations of the present invention may also be formulated with a number of other compounds. These compounds and substances add to the palatability or sensory perception of the particles (e.g., flavorings and colorings) or improve the nutritional value of the particles (e.g., minerals, vitamins, phytonutrients, antioxidants, etc.).

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandrosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In further embodiments, the lipid formulations comprise at least one food flavoring such as acetaldehyde (ethanal), acetoin (acetyl methylcarbinol), anethole (parapropenyl anisole), benzaldehyde (benzoic aldehyde), N-butyric acid (butanoic acid), d- or l-carvone (carvol), cinnamaldehyde (cinnamic aldehyde), citral (2,6-dimethyloctadien-2,6-al-8, gera-nial, neral), decanal (N-decylaldehyde, capraldehyde, capric aldehyde, caprinaldehyde, aldehyde C—IO), ethyl acetate, ethyl butyrate, 3-methyl-3-phenyl glycidic acid ethyl ester (ethyl-methyl-phenyl-glycidate, strawberry aldehyde, C-16 aldehyde), ethyl vanillin, geraniol (3,7-dimethyl-2,6 and 3,6-octadien-1-ol), geranyl acetate (geraniol acetate), limonene (d-, 1-, and dl-), linalool (linalol, 3,7-dimethyl-1,6-octadien-3-ol), linalyl acetate (bergamol), methyl anthranilate (methyl-2-aminobenzoate), piperonal (3,4-methylenedioxy-benzaldehyde, heliotropin), vanillin, alfalfa (Medicago sativa L.), allspice (Pimenta officinalis), ambrette seed (Hibiscus abelmoschus), angelic (Angelica archangelica), Angostura (Galipea officinalis), anise (Pimpinella anisum), star anise (Illicium verum), balm (Melissa officinalis), basil (Ocimum basilicum), bay (Laurus nobilis), calendula (Calendula officinalis), (Anthemis nobilis), capsicum (Capsicum frutescens), caraway (Carum carvi), cardamom (Elettaria cardamomum), cassia, (Cinnamomum cassia), cayenne pepper (Capsicum frutescens), Celery seed (Apium graveolens), chervil (Anthriscus cerefolium), chives (Allium schoenoprasum), coriander (Coriandrum sativum), cumin (Cuminum cyminum), elder flowers (Sambucus canadensis), fennel (Foeniculum vulgare), fenugreek (Trigonella foenum-graecum), ginger (Zingiber officinale), horehound (Marrubium vulgare), horseradish (Armoracia lapathifolia), hyssop (Hyssopus officinalis), lavender (Lavandula officinalis), mace (Myristica fragrans), marjoram (Major ana hortensis), mustard (Brassica nigra, Brassica juncea, Brassica hirta), nutmeg (Myristica fragrans), paprika (Capsicum annuum), black pepper (Piper nigrum), peppermint (Mentha piperita), poppy seed (Papayer somniferum), rosemary (Rosmarinus officinalis), saffron (Crocus sativus), sage (Salvia officinalis), savory (Satureia hortensis, Satureia montana), sesame (Sesamum indicum), spearmint (Mentha spicata), tarragon (Artemisia dracunculus), thyme (Thymus vulgaris, Thymus serpyllum), turmeric (Curcuma longa), vanilla (Vanilla planifolia), zedoary (Curcuma zedoaria), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron and turmeric).

In still further embodiments, the compositions comprise at least one phytonutrient (e.g., soy isoflavonoids, oligomeric proanthcyanidins, indol-3-carbinol, sulforaphone, fibrous ligands, plant phytosterols, ferulic acid, anthocyanocides, triterpenes, conjugated fatty acids such as conjugated linoleic acid and conjugated linolenic acid, polyacetylene, quinones, terpenes, cathechins, gallates, and quercitin). Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, *Ginkgo Biloba*, red clover, burdock root, dandelion, parsley, rose hips, milk thistle, ginger, Siberian ginseng, rosemary, curcumin, garlic, lycopene, grapefruit seed extract, spinach, and broccoli.

In still other embodiments, the compositions comprise at least one vitamin (e.g., vitamin A, thiamin (B1), riboflavin (B2), pyridoxine (B6), cyanocobalamin (B12), biotin, ascorbic acid (vitamin C), retinoic acid (vitamin D), vitamin E, folic acid and other folates, vitamin K, niacin, and pantothenic acid). In some embodiments, the particles comprise at least one mineral (e.g., sodium, potassium, magnesium, calcium, phosphorus, chlorine, iron, zinc, manganese, fluorine, copper, molybdenum, chromium, selenium, and iodine). In some particularly preferred embodiments, a dosage of a plurality of particles includes vitamins or minerals in the range of the recommended daily allowance (RDA) as specified by the United States Department of Agriculture. In still other embodiments, the particles comprise an amino acid supplement formula in which at least one amino acid is included (e.g., 1-carnitine or tryptophan).

The present invention likewise provides methods of using the lipid formulations. These methods and uses are described in detail below but may be summarized as follows. In some embodiments, the present invention provides methods of treating a subject comprising administering to the subject the bioactive lipid formulation or oral delivery vehicle, food product, nutritional supplement, dietary supplement or functional food comprising the lipid formulation to a subject in need thereof. In some embodiments, the administration is oral, topical, parenteral, enteral, transdermal, intradermal, intraocular, intravitreal, sublingual, or intravaginal and may preferably comprise an effective amount of the composition.

In further preferred embodiments, the present invention provides methods of reducing obesity, inducing weight loss, increasing lean body mass, increasing muscularity, increasing muscle mass, improving body composition, alleviating one or more symptoms metabolic syndrome, treating diabetes, decreasing insulin resistance, reducing inflammation, improving concentration, memory, cognitive function, attention and treating, alleviating or improving one or more of the following diseases or conditions: restenosis, arteriosclerosis, coronary heart disease, thrombosis, myocardial infarction, stroke, hypertension, fatty liver, diabetes, hyperglycaemia, hyperinsulinemia, and stenosis, rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myasthenia gravis), various cardiovascular disorders (e.g. myocarditis, congestive heart failure, arteriosclerosis and stable and unstable angina, and Wegeners granulomatosis), inflammatory bowel diseases and colitis (e.g., Crohn's colitis), nephritis, various inflammatory skin disorders (e.g. psoriasis, atopic dermatitis and food allergy) and acute and chronic allograft rejection after organ transplantation, comprising administering to a subject in need thereof the bioactive lipid composition, structured phospholipid composition or structured acylglyceride composition or oral delivery vehicle, food product, nutritional supplement, dietary supplement or function food as described above. In some embodiments, the administration or oral, topical, parenteral, enteral, transdermal, intradermal, intraocular, intravitreal, sublingual, or intravaginal and may preferably comprise an effective amount of the composition. The treatment is preferably performed under conditions such that the disease or condition is alleviated or improved as compared to an untreated state.

The present technology relates to the use of a composition according to embodiments of the technology for the manufacture of a medicament for the treatment and/or prevention of a condition selected from diabetes, inflammatory disorders, metabolic syndrome, obesity, hypertension, fatty liver, diabetes, hyperglycaemia, hyperinsulinemia, and stenosis.

In some embodiments, the present technology provides use of a compound according to the technology for the manufacture of a medicament for lowering concentration of cholesterol and triglycerides in the blood of mammals and/or inhibiting the oxidative modification of low density lipoprotein.

In some embodiments, the present technology provides a method for producing weigh loss or a reduction of the fat mass in a human or non-human animal in need thereof, comprising administering thereto an effective amount of a compound of the technology or a pharmaceutically acceptable salt thereof.

In some embodiments, the present technology provides a method for the modification of the fat distribution and content of animals in order to improve the quality of the meat, or product such as milk and eggs, comprising administering thereto an effective amount of a compound of the technology or a pharmaceutically acceptable salt thereof. Preferably the animal is an agricultural animal, such as gallinaceous birds, bovine, ovine, caprine or porcine mammals. The animal may be a fish or shellfish, such as salmon, cod, Tilapia, clams, oysters, lobster or crabs.

In some embodiments, the present technology provides use of a compound according to the technology or a pharmaceutically acceptable salt thereof in the manufacture of a medicament for the inhibition and/or prevention of the growth of tumors.

In some embodiments, the present technology provides use of a compound according to the technology in the manufacture of a medicament for the inhibition and/or prevention of the invasion of a primary tumor into the connective tissue.

In some embodiments, the present technology provides use of a compound according to the technology for the manufacture of a medicament for the inhibition and/or prevention of the metastatic properties of a tumor, e.g., to inhibit the formation of secondary tumors. For example, the use of the present compounds may increase the overall survival of mammals with tumors.

In some embodiments, the present technology provides a method for the treatment and/or inhibition of primary and secondary metastatic neoplasms, comprising administering a compound of the technology or a pharmaceutically acceptable salt thereof.

In some embodiments, the present technology provides use of a compound of the technology or a pharmaceutically acceptable salt thereof in the manufacture of a medicament for the prevention and/or treatment of proliferative skin disorders such as psoriasis, atopic dermatitis, non-specific dermatitis, primary irritant contact dermatitis, allergic contact dermatitis, lamellar ichthyosis, epidermolytic hyperkeratosis, pre malignant sun induced keratosis, and seborrhea.

In some embodiments, the present technology provides use of a compound of the technology or a pharmaceutically acceptable salt thereof in the manufacture of a medicament for the inhibition of proliferation and/or induction of differentiation of keratinocytes.

In some embodiments, the present technology provides use of a compound of the technology or a pharmaceutically acceptable salt thereof in the manufacture of a medicament for the prevention and/or treatment of inflammatory disorders. For example, in some embodiments, the present technology provides use of a compound of the technology or a pharmaceutically acceptable salt thereof in the manufacture of a medicament for the prevention and/or treatment of inflammatory disorders, wherein the inflammatory disorder is selected from the group comprising immune mediated disorders such as rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegeners granulomatosis), inflammatory bowel diseases and colitis (e.g., Crohn's colitis), nephritis, various inflammatory skin disorders (e.g. psoriasis, atopic dermatitis and food allergy) and acute and chronic allograft rejection after organ transplantation.

In some embodiments, the present technology provides a method for enhancing the endogenous production of interleukin-10 (IL-10) in mammalian cells or tissues, comprising administering a compound of the technology or a pharmaceutically acceptable salt thereof. In some embodiments, the mammal has developed or is susceptible to develop an autoimmune and/or inflammatory disorder.

In some embodiments, the present technology provides a method for suppression of the endogenous production of interleukin-2 (IL-2) in mammalian cells or tissues, comprising administering a compound of the technology or a pharmaceutically acceptable salt thereof. In some embodiments, the mammal has developed or is susceptible to develop an autoimmune and/or inflammatory disorder.

In some embodiments, the present technology provides use of a compound of the technology or a pharmaceutically acceptable salt thereof in the manufacture of a medicament for the inhibition of proliferation of stimulated peripheral mononuclear cells (PBMC).

In some embodiments, the methods comprise co-administration of a delta-6 desaturase inhibitor, particularly where the lipid formulations comprise 5,11,14-eicosatrienoic acid and 11, 14 eicosadienoic acid (20:2 n-6). The present invention is not limited to any particular delta-6 desaturase inhibitor. In some embodiments, the delta-6 desaturase inhibitor is 2,2-diphenyl-5-(4-[[(1 E)-pyridin-3-yl-methylidene]amino]piperazin-1-yl)pentanenitrile (SC-26196.

Further description of these and other diseases is provided below.

Obesity and Related Diseases

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, Acanthosis nigricans, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease.

In some embodiments, the present technology provides a treatment regimen that is useful in returning the body weight of obese subjects toward a normal body weight. In some embodiments, the technology provides a therapy for obesity that results in maintenance of the lowered body weight for an extended period of time. Further, in some embodiments the present technology reduces or inhibits the weight gain normally induced by fat rich diets.

In some embodiments, the present technology prevents obesity and, once treatment has begun, to arrests progression or prevents the onset of diseases that are the consequence of, or secondary to, the obesity, such as hypertension and fatty liver.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficiency, normal variant short stature, Turner's syndrome, and other pathological conditions showing reduced metabolic activity.

In some embodiments, the present technology provides a treatment regimen that is useful in lowering the blood pressure. Further, in some embodiments the present technology provides a treatment regimen that is useful in lowering the concentration of triacylglycerols in the liver. It is anticipated that such a regimen provides an inhibiting effect on the development of a fatty liver condition and is suited as a method for the treatment of the manifested disease.

In some embodiments, the compounds of the present technology activate the oxidation, and also reduce the concentration, of triglycerides in the liver.

The term "metabolic syndrome" is used to describe a multimetabolic syndrome that is inter alia characterized by hyperinsulinemia, insulin resistance, obesity, glucose intolerance, Type 2 diabetes mellitus, dyslipidemia, or hypertension.

As indicated above it is anticipated that the compounds of the present technology provide a positive effect on all the conditions mentioned above, e.g., by regulating both glucose and lipid homeostasis, and thus it is anticipated that the compounds of the present technology are suitable agents for the regulation of the above defined metabolic disease (sometimes called syndrome X).

Diabetes

There are two major forms of diabetes mellitus. One is type I diabetes, which is also known as insulin-dependent diabetes mellitus (IDDM), and the other is type II diabetes, which is also known as noninsulin-dependent diabetes mellitus (NIDDM). Most patients with IDDM have a common pathological picture; the nearly total disappearance of insulin-producing pancreatic beta cells which results in hyperglycemia.

Considerable evidence has been accumulated showing that most IDDM is the consequence of progressive beta-cell destruction during an asymptomatic period often extending over many years. The prediabetic period is recognized usually by the detection of circulating islet-cell autoantibodies and insulin autoantibodies.

As such, there is a need for a compound that is nontoxic and has no or minimal side effects but that would prevent clinical IDDM and NIDDM.

Type I diabetes: severe diabetes mellitus, usually of abrupt onset prior to maturity, characterized by low plasma insulin levels, polydipsia, polyuria, increased appetite, weight loss and episodic ketoacidosis; also referred to as IDDM.

Type II diabetes: an often mild form of diabetes mellitus, often of gradual onset, usually in adults, characterized by normal to high absolute plasma insulin levels which are relatively low in relation to plasma glucose levels; also referred to as NIDDM.

Type I and II diabetes are in accordance with an etiologic classification considered as primary diabetes respectively.

Secondary diabetes comprises pancreatic, extrapancreatic and/or endocrine or drug-induced diabetes. Further, some types of diabetes are classified as exceptional forms. These include lipoatrophic, myatonic diabetes, and a type of diabetes caused by disturbance of insulin receptors.

Considering the high prevalence of diabetes in our society and the serious consequences associated therewith as discussed above, any therapeutic drug potentially useful for the treatment and prevention of this disease would have a profound beneficial effect on their health. There is a need in the art for a drug that reduces the concentration of glucose in the blood of diabetic subjects without significant adverse side effects.

Accordingly, in some embodiments, the present technology provides a treatment regimen that is useful in lowering the blood glucose and to treat a diabetic condition. Moreover, in some embodiments, the present technology provides a treatment regimen that is useful in lowering the concentration of insulin in the blood, and to increase the effect of the remaining insulin. In some preferred embodiments, the compositions of the present invention are useful for ameliorating the symptoms of diabetes, providing nutritional support to a subject with diabetes, promoting healthy blood sugar levels, supporting efficient insulin production and secretion, and/or supporting healthy glucose metabolism.

Stenosis

Many pathological conditions have been found to be associated with smooth muscle cell proliferation. Such conditions include restenosis, arteriosclerosis, coronary heart disease, thrombosis, myocardial infarction, stroke, smooth muscle neoplasms such as leiomyoma, and leiomyosarcoma of the bowel and uterus and uterine fibroid or fibroma.

Over half a million interventional intravascular procedures are performed each year. While such invasive procedures continue to improve over time, as many as 30% to 50% of the procedures performed each year fail as a result of restenosis, e.g., the formation of secondary stenosis. The reduction of restenosis is, therefore, often cited as the most critical factor in increasing the success realized in the treatment of cardiovascular disease through the use of interventional intravascular procedures, such as angioplasty, atherectomy, and procedures utilizing stents, and laser technology.

In balloon angioplasty, e.g. Percutaneous Transluminal Coronary Angioplasty (PTCA), a small incision is made to an artery in the patient's leg or arm and a long hollow tube, called a guide catheter, is inserted into the artery. A thick guide wire and deflated balloon catheter are then inserted into the guide catheter and are carefully advanced through the patient's blood vessels using X-ray visualization. The deflated balloon is advanced until it reaches the site of the luminal narrowing, at which point the physician inflates the balloon one or more times to a pressure of about 4-6 atm for about 60 seconds. When inflated, the balloon cracks and fractures the plaque and stretches the muscle fiber in the artery wall beyond its ability to recoil completely. Although no plaque is removed in this procedure, the fracturing of the plaque and the stretching of the arterial wall increase the vessel lumen, thereby allowing for increased blood flow.

The restenosis that accompanies such procedures is characterized by platelet aggregation and adhesion, smooth muscle cell proliferation, narrowing of the vessel lumen, restricted vasodilatation, and an increase in blood pressure. Smooth muscle cells in the intimal layer of the artery have been reported to enter the growth cycle within about 2-3 days of these procedures and to proliferate for several days thereafter (intimal hyperplasia).

Compounds that reportedly suppress smooth muscle proliferation in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation.

As is apparent from the foregoing, many problems remain to be solved in the use of inhibitory drugs to effectively treat smooth muscle cell mobilization and proliferation. It would be highly advantageous to develop new compositions or methods for inhibiting stenosis, restenosis or related disorders due to proliferation and mobilization of vascular smooth muscle cells following, for example, traumatic injury to vessels rendered during vascular surgery.

Accordingly, it is anticipated that embodiments of compounds in accordance with the present technology are effective in the treatment of these diseases.

Tumors

The development of new and more effective chemotherapeutic agents for cancer treatment requires considering a variety of factors including cytotoxicity, tumor cell proliferation, invasion, and metastasis. Conventional anticancer agents have typically been identified on the basis of their cytotoxicity alone.

Tumor progression is thought to occur when variant cells having selective growth properties arise within a tumor cell population, and one of the final stages of tumor progression is the appearance of the metastatic phenotype.

During metastasis, the tumor cells invade the blood vessels, survive against circulating host immune defenses, and then extravasate, implant, and grow at sites distant from the primary tumor. This ability of tumor cells to invade neighboring tissues and to colonize other organs is among the leading causes of cancer related deaths.

The term metastasis encompasses a number of phenotypic traits that together result in the clinical problem that most often leads to death from cancer. The cells lose their adherence and restrained position within an organized tissue, move into adjacent sites, develop the capacity both to invade and to egress from blood vessels, and become capable of proliferating in unnatural locations or environments. These changes in growth patterns are accompanied by an accumulation of biochemical alterations that have the capacity to promote the metastatic process.

So far, little is known about the intrinsic mechanism involved in the metastatic cascade. It is likely that in some cases the augmented metastatic potential of certain tumor cells may be due to an increased expression of oncogenes, which normally are responsible for control of various cellular functions, including differentiation, proliferation, cell motility, and communication. Further, it has been shown that substances that modulate signal transduction pathways can inhibit the metastatic behavior of a tumor, and it is also speculated that compounds with surface related effects, e.g., compounds that modulates the cell membranes, might be involved in the process leading to metastasis.

Cancer is a disease of inappropriate tissue accumulation. This derangement is most evident clinically when tumor tissue bulk compromises the function of vital organs. Contrary to what is generally thought, human malignant disorders are usually not diseases of rapid cell proliferation. In fact, the cells of most common cancers proliferate more slowly than many cells in normal tissues. It is a relatively slow accumulation of tumor tissue within vital organs that proves fatal to most patients who die of cancer.

Chemotherapeutic agents share one characteristic: they are usually more effective in killing or damaging malignant cells than normal cells. However, the fact that they do harm normal cells indicates their potential for toxicity. Nearly all chemotherapeutic agents currently in use interfere with DNA synthesis, with the provision of precursors for DNA and RNA synthesis, or with mitosis. Such drugs are most effective against cycling cells. The mechanism of cell death after treatment with any single agent or combination of agents is complex and is likely to include more than one process. Because most clinically detectable tumors are composed mostly of non-cycling cells, it is not surprising that chemotherapy is not always effective in eradicating cancer.

The strategy of cancer treatment is to shift tumor cells from a non-cycling compartment to a cycling compartment. Several methods that promote this shift form the basis for combined-modality treatment. Surgery is most commonly used to reduce tumor size and thus facilitate re-entry of cancer cells into the cell cycle. After the primary tumor is completely removed, microscopic metastases may remain at distant sites. Because of their small size, the micrometastases are composed principally of cycling cells. Small numbers of cells that remain at primary tumor site are also likely to re-enter the cell cycle. Thus, the remaining cancer cells are often susceptible to chemotherapy. Radiation therapy or chemotherapy alone can also be used to reduce tumor bulk and thus recruit cells into the cycling cell compartment.

Combination drug therapy is, therefore, the basis for most chemotherapy employed at present. Combination chemotherapy uses the different mechanisms of action and cytotoxic potentials of multiple drugs. However, even though the chemotherapeutic agents are more effective in killing or damaging malignant cells than normal cells, the fact that they do harm normal cells indicates their great potential for toxicity. For chemotherapy to be effective, the patient must be in good physiologic condition.

Cancer treatment requires inhibition of a variety of factors including tumor cell proliferation, metastatic dissemination of cancer cells to other parts of the body, invasion, tumor-induced neovascularization, and enhancement of host immunological responses and cytotoxicity.

Conventional cancer chemotherapeutic agents have often been selected on the basis of their cytotoxicity to tumor cells. However, some anticancer agents have adverse effects on the patient's immunological system. Unfortunately, for the vast majority of conventional antineoplastic agents the margin between an effective dose and a toxic dose, e.g., the therapeutic index, is extremely low. Thus, it would be greatly advantageous if a cancer therapy or treatment could be developed that would afford noncytotoxic protection against factors that might lead to growth, progression and metastasis of invasive cancers.

Accordingly, in some embodiments, the present technology provides a method for the prevention and/or treatment of primary and metastatic neoplasms that involves using a fatty acid analogue, or a lipid comprising a fatty acid analogue, of the present technology to treat a patient suffering from a cancer.

The two essential features of cancer are invasion and metastasis. At one extreme, microinvasion of the basement membrane characterizes the transition from neoplasia to cancer, and at the other extreme, metastases generally lead to death. Invasion into the underlying connective tissue by primary tumor proceeds in stages and is facilitated by various mediators produced by the tumor cells. Tumor cells that have not invaded the basement membrane and remain confined within the epithelium are termed carcinoma in situ. Metastases, on the other hand, may form when circulating tumor cells with adherent lymphocytes and platelets are trapped in capillaries and the tumor cell membrane interacts with the capillary endothelium. The capillary endothelial junctions retract, and tumor cell ligands bind to receptors on the endothelial and basement membranes.

Tumor cells then release collagenase IV, which destroys collagen IV, a major component of the underlying basement membrane. Invasion of the subcapillary connective tissue is aided by binding to the glycoproteins laminin and fibronectin, by the release of proteases that destroy the matrix, and by the secretion of motility and chemotactic factors. Tumor cells then may proliferate and synthesise platelet aggregatory factors such as thromboxanes and procoagulants, thereby leading to the deposition of a fibrin cocoon around the cells. Such a cocoon may protect the micrometastasis from attack by the host's immune system.

Cancers that can be prevented and/or treated by the compositions and methods of the present technology include, but are not limited to, human sarcomas and carcinomas, e.g. carcinomas, e.g., colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Specific examples of such cancers are described in the sections below.

Skin Disorders

Proliferative skin diseases are widespread throughout the world and afflict millions of humans and their domesticated animals. Proliferative skin diseases are characterized by keratinocyte cell proliferation, or division, and may also be associated with incomplete epidermal differentiation. Psoriasis is the most serious of the proliferative skin diseases with which this technology is concerned.

Psoriasis is a genetically determined disease of the skin characterized by two biological hallmarks. First, there is a profound epidermal hyperproliferation related to accelerated and incomplete differentiation. Second, there is a marked inflammation of both epidermis and dermis with an increased recruitment of T lymphocytes, and in some cases, formation of neutrophil microabcesses. Many pathologic features of psoriasis can be attributed to alterations in the growth and maturation of epidermal keratinocytes, with increased proliferation of epidermal cells, occurring within 0.2 mm of the skin's surface.

Traditional investigations into the pathogenesis of psoriasis have focused on the increased proliferation and hyperplasia of the epidermis. In normal skin, the time for a cell to move from the basal layer through the granular layer is 4 to 5 weeks. In psoriatic lesions, the time is decreased sevenfold to tenfold because of a shortened cell cycle time, an increase in the absolute number of cells capable of proliferating, and an increased proportion of cells that are actually dividing. The hyperproliferative phenomenon is also expressed, although to a substantially smaller degree, in the clinically uninvolved skin of psoriatic patients.

A common form of psoriasis, psoriasis vulgaris, is characterized by well-demarcated erythematous plaques covered by thick, silvery scales. A characteristic finding is the isomorphic response (Koebner phenomenon), in which new psoriatic lesions arise at sites of cutaneous trauma. Lesions are often localized to the extensor surfaces of the extremities, and the nails and scalp are also commonly involved.

Therapeutic efforts in psoriasis are aimed at decreasing the proliferative rate of the epidermis, either by direct action on cell division or indirectly by reducing the immunological response. For patients with localized, limited psoriasis, administration of topical corticosteroids is the most convenient outpatient therapy.

Rapid improvement may be seen with this approach, but the beneficial short-term efficacy is limited and chronic topical corticosteroid treatment is not advisable. Side effects from chronic topical corticosteroid therapy can include atrophy of the skin, development of tolerance to the agent used (tachyphylaxis), and serious exacerbation of the disease after discontinuation. Pituitary-adrenal suppression is a potential and serious complication of potent topical corticosteroid therapy, particularly when the agent covers a large portion of the body surface and is used under occlusive dressings.

The retinoids, particularly etretinate, either alone or in combination with PUVA, are also an effective treatment for psoriasis. Etretinate is especially useful in the exfoliative and pustular varieties of psoriasis. However, several major potential complications must be monitored in patients placed on retinoids. As a class, the retinoids are potent teratogens and should not be given to women of childbearing age who are not using adequate contraception.

Etretinate, like other retinoids, can produce elevations in cholesterol and triglyceride levels; therefore dietary regulation may be necessary. In addition, because etretinate can induce hepatotoxicity, liver function tests should be performed before and at regular intervals during use of the drug.

Considering the complications and side effects attendant to the use of different drugs and photochemotherapy currently used in treating a skin proliferative disease such as psoriasis, there is a need for a new method and a new composition to inhibit keratinocyte proliferation to alleviate the symptoms of skin proliferation diseases.

Inflammatory and Auto-Immune Disorders

Interleukins, interferons, colony stimulating factors and TNF-alpha are examples of a group of diverse multi-functional proteins called cytokines. Cytokines are a class of secreted soluble proteins normally present in very low concentration in a variety of cells. Lymphoid, inflammatory hemopoietic, and other cells such as connective tissue cells (e.g. fibroblasts, osteoblasts) secrete a variety of cytokines which regulate the immune, inflammatory, repair, and acute phase responses by controlling cell proliferation, differentiation, and effector functions. The effects of cytokines are mediated through binding to high affinity receptors on specific cell types.

An important cytokine is IL-10, a 35-40 kDa peptide produced by helper T-cells, B-cells, monocytes, macrophages, and other cell types. In vitro, IL-10 has demonstrated immunosuppressive properties as evidenced by its ability to suppress cytokine production including IL-1 and TNFa. IL-10 also inhibits activation of other inflammatory cytokines, and therefore has potent anti-inflammatory activity.

It has been of recent interest to administer-IL-10 in the treatment of certain conditions characterized by excessive IL-1 and TNF-alpha production. Such diseases or conditions include loosening of prosthetic joint implants, inflammation, diabetes, cancer, graft versus host diseases, viral, fungal and bacterial infections, lipopolysaccharide endotoxin shock, diseases of depressed bone marrow function, thrombocytopenia, osteoporosis, spondyloarthropathies, Paget's disease, inflammatory bowel disease, arthritis, osteoarthritis, autoimmune diseases such as rheumatoid arthritis, systemic lupus erythematosus, and connective tissue diseases.

For example, purified IL-10 has been shown in vitro to suppress certain types of viral infections. U.S. Pat. No. 5,665,345 discloses a method for inhibiting replication of the human immunodeficiency virus, retro-viruses, and Kaposi sarcoma in human cells by administering IL-10.

IL-10 has also been suggested for use in the treatment of certain cancers. U.S. Pat. No. 5,570,190 discloses administering exogenous IL-10 to treat mammals suffering from acute myelogenous leukemia and acute lymphocytic leukemia. IL-10 is said to be administered either in the purified or recombinant form and is believed to inhibit the proliferation of acute leukemia blast cells. Similarly, IL-10 was shown to inhibit bone marrow metastasis in severe combined immunodeficient mice.

The above conventional approaches to treating conditions characterized by excessive IL-1 and TNF-alpha production have been limited to administering exogenous purified or recombinant IL-10 intravenously. Since IL-10 is a protein, it is difficult to infuse intravenously into a mammal because proteins often leach out of solution and bind to the plastic or glass used in intravenous administration sets. Also, proteins are often incompatible and precipitate when mixed with physiological solutions such as dextrose or saline. In addition, oral and topical routes are unavailable for IL-10 administration. The oral route is unavailable because protein is degraded in the gastrointestinal tract. None of the above approaches suggests enhancing endogenous IL-10 production in mammals for prophylaxis and treatment of diseases or conditions.

Further, it is known that IL-10 is a powerful deactivator of macrophages and T cells, and inadequate production has been implicated in various autoimmune and inflammatory disorders.

In addition, or in the alternative, embodiments of the compound or composition of the present technology are useful in the treatment of the following disorders: cancer, inflammation or inflammatory disease, dermatological disorders, fever, cardiovascular effects, hemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumor growth, invasion and spread, angiogenesis, metastases, malignant, ascites and malignant pleural effusion; cerebral ischemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, embodiments of the compound or composition of the present technology are useful in the treatment of the following disorders: cytokine and cell proliferation/differentiation activity; immunosuppressant or immunostimulant activity (e.g., for treating immune deficiency, including infection with human immune deficiency virus; regulation of lymphocyte growth; treating cancer and many autoimmune diseases, and to prevent transplant rejection or induce tumor immunity); regulation of hematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilizing specific cell types to sites of injury or infection); hemostatic and thrombolytic activity (e.g. for treating hemophilia and stroke); anti-inflammatory activity (for treating e.g. septic shock or Crohn's disease); as antimicrobials; modulators of e.g. metabolism or behavior; as analgesics; treating specific deficiency disorders; in treatment of e.g. psoriasis, in human or veterinary medicine.

In addition, or in the alternative, embodiments of the composition of the present technology are useful in the treatment of the following disorders: macrophage inhibitory and/or T cell inhibitory activity and thus, anti-inflammatory activity; anti-immune activity, e.g., inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g., retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumor cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Treatment

Embodiments of the technology include any therapeutic application that can benefit a human or non-human animal, for example a mammal. As such, both human and veterinary treatments are within the scope of the present technology.

Treatment may be in respect of an existing condition or it may be prophylactic. It may be of an adult, a juvenile, an infant, a fetus, or a part of any of the aforesaid (e.g., an organ, tissue, cell, or nucleic acid molecule).

In some embodiments, an active agent for use in treatment is administered via any appropriate route and at any appropriate dosage. Dosages can vary between wide limits, depending upon the nature of the treatment, the age and condition of the individual to be treated, etc., and a physician will ultimately determine appropriate dosages to be used. However, without being bound by any particular dosages, a daily dosage of a compound of the present technology of from 1 µg to 1 mg/kg body weight may be suitable. The dosage may be repeated as often as appropriate. If side effects develop, the amount and/or frequency of the dosage can be reduced, in accordance with good clinical practice.

I claim:

1. A lipid formulation comprising an effective amount of 5,11,14-eicosatrienoic acid, wherein said lipid formulation is suitable for human consumption, the formulation comprises 11, 14-eicosadienoic acid (20:2 n-6), wherein the ratio of 5,11,14-eicosatrienoic acid to 11, 14-eicosadienoic acid (20:2 n-6) is from 1:1 to 2.5:1, and the formulation comprises an antioxidant from a source different from the source of the 5,11,14-eicosatrienoic acid.

2. The lipid formulation of claim 1, wherein the lipid formulation is provided in a soft gel capsule.

3. The lipid formulation of claim 1, wherein the lipid formulation further comprises at least one topical excipient.

4. The lipid formulation of claim 3, wherein the topical excipient is selected from the group consisting of mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, and benzyl alcohol.

5. The lipid formulation of claim 1, wherein the 5,11,14-eicosatrienoic acid and 11,14-eicosadienoic acid are provided in the formulation as free fatty acids.

6. The lipid formulation of claim 1, wherein the 5,11,14-eicosatrienoic acid and 11,14-eicosadienoic acid provided in the formulation are esterified.

7. The lipid formulation of claim 1, further comprising 7,11, 14-eicosatrienoic acid.

* * * * *